(12) United States Patent
Endou

(10) Patent No.: US 10,101,314 B2
(45) Date of Patent: Oct. 16, 2018

(54) STATE MONITORING DEVICE OF CUTTING FLUID USING ODOR SENSOR

(71) Applicant: FANUC Corporation, Yamanashi (JP)

(72) Inventor: Takahiro Endou, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 0 days.

(21) Appl. No.: 14/880,320

(22) Filed: Oct. 12, 2015

(65) Prior Publication Data

US 2016/0109426 A1    Apr. 21, 2016

(30) Foreign Application Priority Data

Oct. 17, 2014 (JP) .................................. 2014-212509

(51) Int. Cl.
  *G01N 33/28*    (2006.01)
(52) U.S. Cl.
  CPC ................................ *G01N 33/2888* (2013.01)
(58) Field of Classification Search
  CPC . G01N 33/2888; G01N 33/2894; G01N 33/30
  See application file for complete search history.

(56) References Cited

U.S. PATENT DOCUMENTS

| | | | | |
|---|---|---|---|---|
| 4,688,355 A | * | 8/1987 | Menigat ................. | G01M 1/323 451/28 |
| 4,873,904 A | * | 10/1989 | Norimatsu ............. | G10H 3/188 84/722 |
| 5,939,650 A | * | 8/1999 | Higuerey ................. | B23H 1/08 219/69.14 |
| 6,153,566 A | | 11/2000 | Yonekura et al. | |
| 6,421,588 B1 | * | 7/2002 | Janata ................. | B60R 16/0234 340/438 |
| 7,282,660 B2 | * | 10/2007 | Kawahara ................ | B23H 1/10 219/69.12 |
| 2004/0075448 A1 | * | 4/2004 | Lvovich ............ | G01N 33/2888 324/707 |
| 2005/0082472 A1 | * | 4/2005 | Dahms ................. | G01N 27/622 250/287 |

(Continued)

FOREIGN PATENT DOCUMENTS

| | | |
|---|---|---|
| JP | 6-75638 U | 10/1994 |
| JP | 8-302379 A | 11/1996 |

(Continued)

OTHER PUBLICATIONS

Decision to Grant a Patent in JP Application No. 2014-212509, dated Jun. 13, 2017.

(Continued)

*Primary Examiner* — Son Le
*Assistant Examiner* — Marrit Eyassu
(74) *Attorney, Agent, or Firm* — Hauptman Ham, LLP

(57) ABSTRACT

When machining a workpiece by a machine tool by cutting, a cutting fluid is sprayed to a workpiece machining region. Above a surface of the cutting fluid in a cutting fluid tank, an odor sensor for detecting the odor emitted by the cutting fluid is disposed in the space defined the surface of the cutting fluid in the cutting fluid tank and a cover. Based on the odor detected by the odor sensor, deterioration of the cutting fluid is determined.

6 Claims, 2 Drawing Sheets

(56) References Cited

U.S. PATENT DOCUMENTS

| | | | | |
|---|---|---|---|---|
| 2009/0111723 A1* | 4/2009 | Shibata | ............... | B23H 1/08 |
| | | | | 508/463 |
| 2010/0312456 A1* | 12/2010 | Nishimura | ............ | F02D 35/023 |
| | | | | 701/103 |
| 2010/0313630 A1* | 12/2010 | Grozinger | ............. | B23Q 17/00 |
| | | | | 73/23.34 |
| 2011/0303210 A1* | 12/2011 | Grumbine | ............. | B28D 5/007 |
| | | | | 125/21 |
| 2014/0007657 A1* | 1/2014 | Matsubara | ............ | G01M 13/04 |
| | | | | 73/53.05 |
| 2014/0262957 A1* | 9/2014 | Gong | ................ | G01N 33/2823 |
| | | | | 208/291 |

FOREIGN PATENT DOCUMENTS

| | | |
|---|---|---|
| JP | 2002-167594 A | 6/2002 |
| JP | 2004-160564 A | 6/2004 |
| JP | 2010-188480 A | 9/2010 |
| JP | 2010188480 A * | 9/2010 |

OTHER PUBLICATIONS

Office Action in JP Application No. 2014-212509, dated Feb. 14, 2017.

* cited by examiner

STATE MONITORING DEVICE OF CUTTING FLUID USING ODOR SENSOR

RELATED APPLICATIONS

The present application claims priority to Japanese Application Number 2014-212509, filed Oct. 17, 2014, the disclosure of which is hereby incorporated by reference herein in its entirety.

BACKGROUND OF THE INVENTION

1. Field of the Invention

The present invention relates to a state monitoring device that monitors the deterioration state of a cutting fluid used when a workpiece is subjected to cutting by a machine tool.

2. Description of the Related Art

Some of machine tools are provided with a cutting-fluid supplying mechanism for carrying out cooling of a tool, removal of chips, lubrication, cleaning upon tool replacement, etc. by spraying a cutting fluid to a cutting region when a workpiece is subjected to cutting. In the cutting-fluid supplying mechanism, the cutting fluid is circulated and repeatedly used. Therefore, impurities such as lubricant oil and microorganisms which cause corrosion are mixed in the cutting fluid, the cutting fluid is deteriorated, and processing is adversely affected as cooling performance reduction, lubrication performance reduction, etc.

As a method for avoiding such adverse effects, Japanese Patent Application Laid-Open No. 2010-188480 (JP 2010-188480 A) describes a monitoring method of monitoring the fluid quality of a cutting fluid, in which a pH sensor, a water-hardness sensor and a concentration sensor are provided to detect the pH value, water hardness and concentration of the cutting fluid, thereby distinguishing the detection values thereof. As a result of that, if the detection values are determined to be within a predetermined normal-value range, a display screen indicative of a normal state is displayed, but if the detection values are determined to be within a caution range, warning is displayed on a display screen, and if the detection values are determined to be in an abnormal range, cutting is prohibited.

Moreover, Japanese Utility Model Publication No. 6-75638 (JP 6-75638 U) describes a cutting-fluid managing device configured to prevent deterioration caused by corrosion of a cutting fluid by pumping up the cutting fluid in a cutting-fluid tank by a pump, heating the cutting fluid by a heater, and killing septic organisms mixed in the cutting fluid, and measure the fluid concentration of the cutting fluid by means of a concentration sensor in order to keep the concentration of the cutting fluid constant by mixing undiluted liquid of the cutting fluid or dilution water in consideration of the measurement result, thereby returning the cutting liquid to the cutting-fluid tank.

When the cutting fluid is deteriorated, cooling performance is reduced and lubrication performance is also reduced, as a result, cutting is adversely affected. Moreover, if the cutting fluid is corroded, all the cutting fluid has to be replaced, and the processes in a factory are temporarily stopped. Furthermore, septic odor is also generated, which leads to deterioration of a working environment.

As a method of detecting deterioration of the cutting fluid, the above-described conventional techniques use the pH sensor, the water-hardness sensor, and the concentration sensor. However, there is a problem that these sensors are affected by the cutting fluid or the impurities mixed in the cutting fluid, the sensor capability is reduced, and it becomes difficult to precisely detect the fluid quality of the cutting fluid.

SUMMARY OF THE INVENTION

Therefore, it is an object of the present invention to provide a cutting-fluid monitoring device capable of reducing the adverse effects on the sensor capability exerted by the cutting fluid or the impurities mixed in the cutting fluid and promptly detecting deterioration of the cutting fluid.

The present invention focuses on the odor generated from the cutting fluid if impurities are mixed in the cutting fluid or if the cutting fluid is corroded, and a change in the type of the odor or odor intensity (strength of odor) is detected by an odor sensor so as to monitor the state of the cutting fluid.

In a first phase of a state monitoring device of a cutting fluid of a machine tool according to the present invention, the machine tool includes a cutting-fluid supplying mechanism circulating and repeatedly supplying the cutting fluid to a region where a workpiece is subjected to cutting. The state monitoring device of the cutting fluid includes: an odor sensor that detects a type of odor of the cutting fluid; and a cutting-fluid deterioration handling unit that carries out a cutting-fluid deterioration handling process when an odor detection signal is output from the odor sensor.

In a second phase of a state monitoring device of a cutting fluid of a machine tool according to the present invention, the machine tool includes a cutting-fluid supplying mechanism circulating and repeatedly supplying the cutting fluid to a region where a workpiece is subjected to cutting. The state monitoring device of the cutting fluid comprising: an odor sensor that measures and outputs odor intensity of the cutting fluid; a fluid-quality deterioration determination unit that compares a measured value measured by the odor sensor with a threshold value set in advance in order to determines fluid-quality deterioration of the cutting fluid; and a cutting-fluid deterioration handling unit that carries out a cutting-fluid deterioration handling process based on a determination result of the fluid-quality deterioration determination unit.

The fluid-quality deterioration determination unit may have a threshold-value setting unit that calculates and sets the threshold value based on the measured value measured by the odor sensor for a first time after replacement of the cutting fluid and a threshold-value calculating coefficient set in advance, and may be configured to compare the measured value measured by the odor sensor with the threshold value calculated and set by the threshold-value setting unit and determine the fluid-quality deterioration of the cutting fluid.

The odor sensor may be surrounded by a cover so as to arrange the odor sensor in a space defined by the cover and a surface of the cutting fluid in a cutting-fluid tank in which the cutting fluid is stored.

The present invention enables detection of impurities mixed in the cutting fluid and corrosion of the cutting fluid by the odor generated by the cutting fluid. Therefore, adverse effects on machining such as cooling performance reduction, lubrication performance reduction, etc. of the cutting fluid can be prevented. Furthermore, a measure can be taken before workers feel the odor, and a comfortable working environment can be maintained.

Moreover, since the odor sensor is disposed in the space above the surface of the cutting fluid, the adverse effects from the cutting fluid and the impurities mixed in the cutting fluid are small, deterioration in the sensor capability is small, and mixing of impurities into the cutting fluid and corrosion of the cutting fluid can be precisely and promptly detected.

BRIEF DESCRIPTION OF THE DRAWINGS

The forgoing and other objects and feature of the invention will be apparent from the following description of preferred embodiments of the invention with reference to the accompanying drawings, in which.

DETAILED DESCRIPTION OF THE PREFERRED EMBODIMENTS

Figure 1:
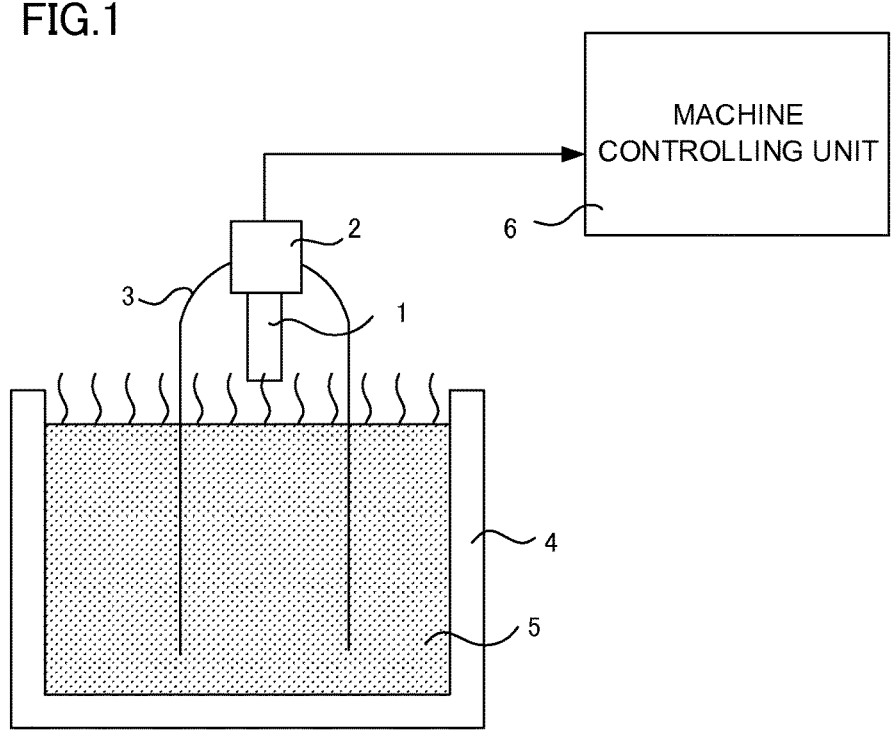
FIG. 1 is an outline drawing of an example of a state monitoring device of a cutting fluid of a machine tool according to the present invention.

An example of a state monitoring device of a cutting fluid of a machine tool according to the present invention will be explained with reference to FIG. 1.

A cutting-fluid tank 4 storing a cutting fluid 5 constitutes part of a cutting-fluid supplying mechanism provided in a machine tool. When the machine tool machines a workpiece by cutting, the cutting fluid 5 stored in the cutting-fluid tank 4 is pumped up by a pump of the cutting-fluid supplying mechanism (not shown), is sprayed to a region for cutting the workpiece, and, after cooling of a tool, etc., removal of chips, cleaning, etc. are carried out, is returned to and stored in the cutting-fluid tank again.

In the present invention, an odor sensor 1 is disposed above a surface of the cutting fluid stored in the cutting-fluid tank 4, a bowl-shaped cover 3 is attached to a sensor head 2 of the odor sensor 1, and the cover 3 is configured to cover the odor sensor 1. The odor sensor 1 is positioned above the surface of the cutting fluid in the cutting-fluid tank 4, an opening of the bowl-shaped cover 3 is configured to enter the cutting fluid 5 stored in the cutting-fluid tank 4, and the odor sensor 1 is configured to be positioned in a space surrounded by the surface of the cutting fluid and the cover 3.

Since the odor sensor 1 is positioned in the space above the surface of the cutting fluid 5 stored in the cutting-fluid tank 4 and is not in the cutting fluid 5, the odor sensor 1 is prevented from being eroded by the cutting fluid, etc. and adversely affecting sensor functions. Moreover, the cutting fluid 5 is emitting odor from its surface, part of the surface is covered with the cover 3, and the odor sensor 1 is disposed in the space defined by the cover 3; therefore, the odor staying in the cover 3 can be efficiently detected by the odor sensor 1. Note that, since the odor sensor 1 detects odor, the odor sensor 1 has to be disposed in the space. However, the cover 3 is not necessarily required, and the odor sensor 1 may be simply disposed above the surface of the cutting fluid 5 stored in the cutting-fluid tank 4.

The odor sensor 1 is connected to a machine controlling unit 6 of a numerical controller which controls the machine tool.

In the present embodiment, a processor and software possessed by the machine controlling unit 6 of the numerical controller constitute part of the cutting-fluid state monitoring device, and the processor of the machine controlling unit 6 reads the output of the odor sensor 1 so as to check deterioration of the cutting fluid, for example, as to whether impurities are mixed in the cutting fluid or not or whether the cutting fluid is corroded or not, based on this detected value.

Figure 2:
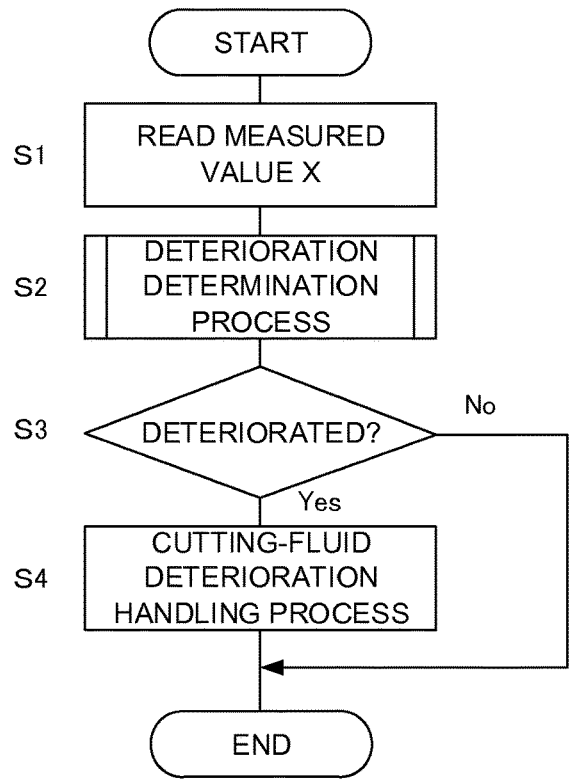
FIG. 2 is a flow chart showing an algorithm of a state monitoring process of the cutting fluid executed by the state monitoring device (a processor of a machine controlling unit) of FIG. 1.

FIG. 2 is a flow chart showing an algorithm of a cutting-fluid state monitoring process carried out for every predetermined cycle by the processor of the machine controlling unit 6 as a function of the cutting-fluid state monitoring device.

When power of the machine tool is turned on and circulating supply of the cutting fluid is started, the processor of the machine controlling unit 6 starts a cutting-fluid state monitoring process shown in FIG. 2 for every predetermined cycle.

First, a measured value X transmitted from the odor sensor 1 is read (step S1), and a cutting-fluid deterioration determination process is carried out based on the read measured value X (step S2). This deterioration determination process will be described later. If it is determined in the deterioration determination process that the cutting fluid is deteriorated (step S3), a cutting-fluid deterioration handling process is carried out (step S4), and the process of the current cycle is terminated. The cutting-fluid deterioration handling process includes: outputting a signal representing that the cutting fluid is deteriorated due to mixing of impurities or corrosion; informing of detection of deterioration of the cutting fluid on a screen of a display device attached to the machine controlling unit 6; stopping an operation of the machine tool; and outputting and displaying the quality of the cutting fluid based on the measured value X.

When it is determined in the deterioration determination process of Step S2 that the cutting fluid is not deteriorated (step S3), the process of the current cycle is terminated without carrying out the cutting-fluid deterioration handling process in step S4.

Figure 3:
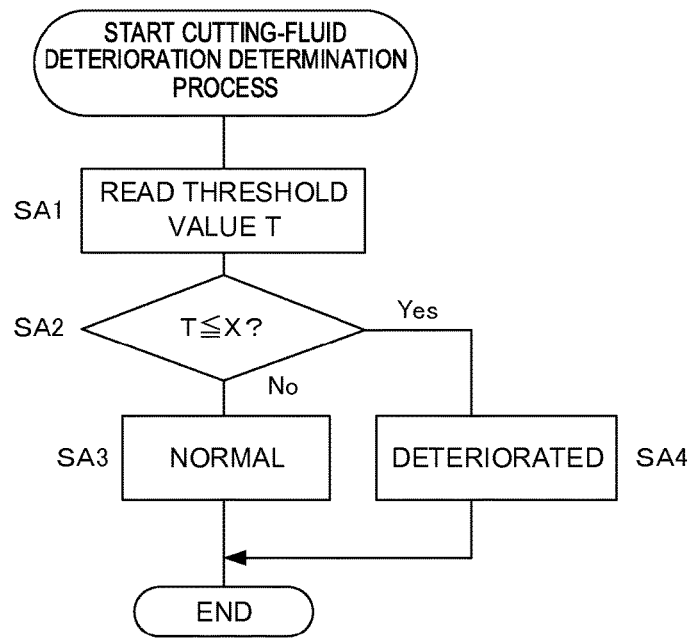
FIG. 3 is a flow chart showing an algorithm of an example of deterioration determination process in step S2 of the flow chart of FIG. 2.

FIG. 3 is a flow chart showing an algorithm of one example of the deterioration determination process of step S2 in the flow chart of FIG. 2.

A threshold value T for determining deterioration of the cutting fluid is set in advance in a memory of the machine controlling unit 6. A value serving as a reference for determining the deterioration of cutting fluid based on the degree of the intensity of odor outputted from the odor sensor 1 is set as the threshold value T. The threshold value T is set in accordance with the type of the cutting fluid and machining conditions such as the material of the workpiece and the degree of machining accuracy. More specifically, the threshold T for determining the deterioration of cutting fluid can be changed and set depending on the cutting fluid to be used and the cutting conditions to be executed, because the correlation between the type and intensity of order generated and the degree of cutting-fluid deterioration is different depending on the type of the cutting fluid, and permissible states of cutting fluid differ depending on the type of workpiece to be cut and machining accuracy such as precision processing or rough processing.

In the deterioration determination process, the processor first reads the threshold value T set and stored in the memory (step SA1), compares the measured odor value X of the output of the odor sensor 1 read in step S1 (see FIG. 2) with the threshold value T (step SA2), and determines whether the measured value X is equal to or higher than the threshold value T or not. As a result of determination, if the measured value X is equal to or higher than the threshold value T (X≥T), the cutting fluid is determined to be deteriorated (step SA4), whereas if the measured value X is smaller than the threshold value T (X<T), the cutting fluid is determined to be normal, not deteriorated (step SA3), whereupon the deterioration determination process is terminated and process proceeds to the main processing (step S3) shown in FIG. 2.

Figure 4:
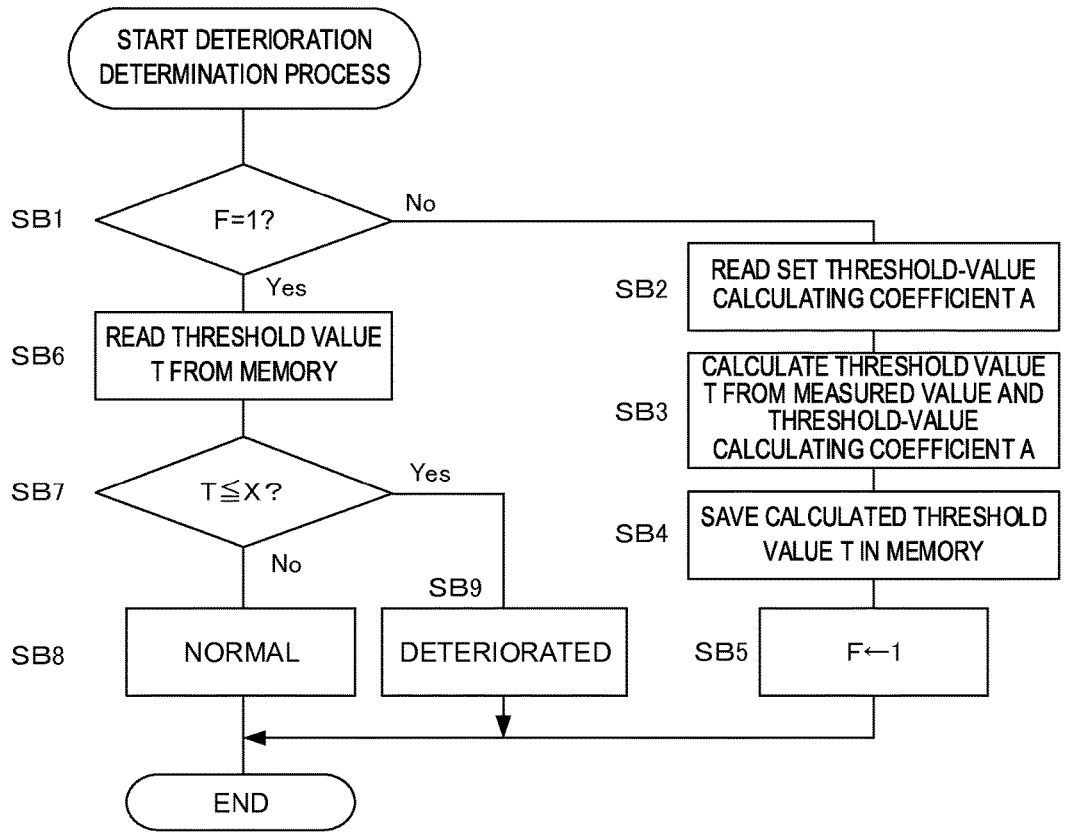
FIG. 4 is a flow chart showing an algorithm of another example of deterioration determination process in step S2 of the flow chart of FIG. 2.

FIG. 4 is a flow chart showing an algorithm of another example of the deterioration determination process of step S2 in the flow chart of FIG. 2.

Even in a state immediately after the cutting fluid is replaced, the odor generated from the cutting fluid is different depending on differences in the concentration of the cutting fluid, the amounts of additives such as an anticorrosion agent and an antifoam agent added to the cutting fluid, and a surrounding usage environment such as temperatures. In view of the above, in this example, cutting-fluid deterioration determination is carried out based on the odor which is measured when the cutting fluid is used for the first time after replacement, and the threshold value T is obtained and set by multiplying the measured odor serving as the base by a threshold-value calculating coefficient A.

The threshold-value calculating coefficient A is changed and set depending on the type of cutting fluid and machining conditions such as the type of workpiece and machining accuracy.

First, when cutting-fluid replacement is executed, determination is made on whether a flag F is reset from "1" to "0" or is set to "1" (step SB1). In a case of the first usage after cutting-fluid replacement, the flag F is reset to "0." Therefore, the process proceeds from step SB1 to step SB2; the set threshold-value calculating coefficient A is read; the threshold value T is calculated by multiplying the measured value X, which has been read in step S1 (see FIG. 2), by the threshold-value calculating coefficient A, in other words, T=A×X is calculated (step SB3); and the calculated threshold value T is set and saved in the memory (step SB4). Then, the flag F is set to "1" (step SB5), and the process returns to the main process of FIG. 2.

From the next processing cycle, since the flag F is set to "1", the process proceeds from step SB1 to step SB6, the set threshold value T is read from the memory, and the measured value X read in step S1 (see FIG. 2) and the threshold value T are compared with each other (step SB7). If it is determined that the measured value X is equal to or higher than the threshold value T, it is determined that the cutting fluid is deteriorated (step SB9). On the other hand, if the measured value X is smaller than the threshold value T, it is determined that the cutting fluid is normal (step SB8), and the process returns to the main process shown in FIG. 2.

In the above described embodiments, the sensor of the type which outputs odor intensity is used as the odor sensor 1, the odor intensity X measured by the odor sensor 1 and the threshold value T are compared with each other so that it is determined that the cutting fluid is deteriorated if the measured value X of the intensity of the odor is equal to or higher than the threshold value T. However, an odor sensor of a type which outputs an odor detection signal (cutting-fluid deterioration signal) when a change in the odor reaches a predetermined level may be used as the odor sensor. If such a sensor is used, a process similar to the process shown in FIG. 2 is carried out for every cycle as the cutting-fluid state monitoring process.

However, this process does not include the cutting-fluid deterioration determination process of step S2 in FIG. 2 (and therefore this process does not include the processes of FIG. 3 and FIG. 4). Accordingly, in this case, the process of step S1 is a process of simply reading the output of the odor sensor, and the output of the odor sensor which is read is then determined (step S3). As a result of determination, if the output of the odor sensor is not an odor detection signal (not a cutting-fluid deterioration signal), it is not considered that the cutting fluid is deteriorated, and processing for handling the odor is not carried out. On the other hand, if the output of an odor sensor is the odor detection signal (cutting-fluid deterioration signal), it is determined that the cutting fluid is deteriorated, and the cutting-fluid deterioration handling process (step S4) is carried out, and the process of the current cycle is terminated.

The present invention is characterized by detection of deterioration of the cutting fluid such as mixing of impurities into cutting fluid or corrosion of cutting fluid by detecting the odor generated from the cutting fluid. When a pH meter or a concentration meter, which detects the fluid quality of the cutting fluid, is further used in combination, a more reliable cutting-fluid managing system can be realized.

The invention claimed is:

1. A state monitoring device of a cutting fluid of a machine tool, the machine tool including a cutting-fluid supplying mechanism circulating and repeatedly supplying the cutting fluid to a region where a workpiece is subjected to cutting, the state monitoring device comprising:
 an odor sensor configured to measure and output odor intensity of the cutting fluid;
 a fluid-quality deterioration determination unit configured to compare a measured odor intensity value measured and output by the odor sensor with a threshold value set in advance in order to determine fluid-quality deterioration of the cutting fluid caused by impurities mixed in the cutting fluid or corrosion of the cutting fluid;
 a cutting-fluid deterioration handling unit configured to carry out a cutting-fluid deterioration handling process in response to a determination result of the fluid-quality deterioration determination unit indicating that the measured odor intensity value is equal to or greater than the threshold value; and
 a cover surrounding the odor sensor and having an opening inside a cutting-fluid tank in which the cutting fluid to be monitored is stored,
 wherein the cover is configured to cover a part of a surface of the cutting fluid stored in the cutting-fluid tank, and
 wherein the odor sensor is arranged in a space defined by the cover and the part of the surface of the cutting fluid to measure the odor intensity of an odor of the cutting fluid in said space.

2. The state monitoring device of the cutting fluid of the machine tool according to claim 1, wherein
 the fluid-quality deterioration determination unit has a threshold-value setting unit configured to calculate and set the threshold value based on
 the measured odor intensity value measured by the odor sensor for a first time after replacement of the cutting fluid, and
 a threshold-value calculating coefficient set in advance.

3. The state monitoring device according to claim 1, wherein the threshold value is changed depending on the cutting fluid and cutting conditions to be executed.

4. The state monitoring device according to claim 1, wherein the cutting-fluid deterioration handling unit is configured to:
 output a signal representing that the cutting fluid is deteriorated due to mixing of impurities or corrosion;

inform of detection of deterioration of the cutting fluid on a screen of a display device attached to a machine controlling unit of the machine tool;

stop an operation of the machine tool; and output and display the quality of the cutting fluid based on the measured odor intensity value measured by the odor sensor.

5. A state monitoring device of a cutting fluid of a machine tool, the machine tool including a cutting-fluid supplying mechanism circulating and repeatedly supplying the cutting fluid to a region where a workpiece is subjected to cutting, the state monitoring device comprising:

an odor sensor configured to measure and output odor intensity of the cutting fluid;

a fluid-quality deterioration determination unit configured to compare a measured odor intensity value measured and output by the odor sensor with a threshold value set in advance in order to determine fluid-quality deterioration of the cutting fluid caused by impurities mixed in the cutting fluid or corrosion of the cutting fluid; and a cutting-fluid deterioration handling unit configured to carry out a cutting-fluid deterioration handling process in response to a determination result of the fluid-quality deterioration determination unit indicating that the measured odor intensity value is equal to or greater than the threshold value, wherein the threshold value is set in accordance with a type of the cutting fluid and machining conditions of the machining tool, wherein the machining conditions include a material of the workpiece and a degree of machining accuracy of the machine tool, wherein the fluid-quality deterioration determination unit has a threshold-value setting unit configured to calculate and set the threshold value based on the measured odor intensity value measured by the odor sensor for a first time after replacement of the cutting fluid, and a threshold-value calculating coefficient set in advance, and wherein the fluid-quality deterioration determination unit is configured to read the set threshold-value calculating coefficient A, calculate the threshold value T by multiplying (i) the measured odor intensity value X measured by the odor sensor at the first time after replacement of the cutting fluid by (ii) the threshold-value calculating coefficient A, as an expression T=A×X, and set and save the calculated threshold value T in a memory.

6. A state monitoring device of a cutting fluid of a machine tool, the machine tool including a cutting-fluid supplying mechanism circulating and repeatedly supplying the cutting fluid to a region where a workpiece is subjected to cutting, the state monitoring device comprising:

an odor sensor configured to detect a type of odor of the cutting fluid;

a cutting-fluid deterioration handling unit configured to carry out a cutting-fluid deterioration handling process in response to an odor detection signal output from the odor sensor; and a cover surrounding the odor sensor and having an opening inside a cutting-fluid tank in which the cutting fluid to be monitored is stored, wherein the cover is configured to cover a part of a surface of the cutting fluid stored in the cutting-fluid tank, and wherein the odor sensor is arranged in a space defined by the cover and the part of the surface of the cutting fluid to detect the type of the odor of the cutting fluid in said space.

* * * * *